United States Patent [19]

Baker et al.

[11] 4,001,430
[45] Jan. 4, 1977

[54] N-T-BUTYL-α-TRICHLOROPHENOX-YBUTYRAMIDES AND THEIR USE AS MITRICIDES

[75] Inventors: Don R. Baker, Orinda; Francis H. Walker, Mill Valley, both of Calif.

[73] Assignee: Stauffer Chemical Company, Westport, Conn.

[22] Filed: June 30, 1975

[21] Appl. No.: 591,728

[52] U.S. Cl. .......................... 424/324; 260/559 B
[51] Int. Cl.² .................. A01N 9/20; A01N 9/24; C07C 103/75
[58] Field of Search .............. 424/324; 260/559 B

[56] References Cited
UNITED STATES PATENTS 3,557,209  1/1971  Richter et al. ................ 260/465 D

*Primary Examiner*—V. D. Turner
*Attorney, Agent, or Firm*—Michael J. Bradley

[57] ABSTRACT

Miticidally active compounds having the generic formula

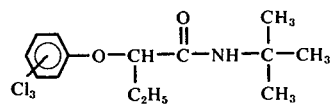

are described herein.

8 Claims, No Drawings

N-T-BUTYL-α-TRICHLOROPHENOXYBUTYRAMIDES AND THEIR USE AS MITRICIDES

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat No. 2,426,885 and its two continuations-in-part, U.S. Pat. Nos. 2,484,295 and 2,484,296. Herbicidal properties of such compounds are taught in U.S. Pat. Nos. 3,272,844, 3,439,018, and 3,564,607, Belgian Pat. No. 739,714, French Pat. No. 1,600,445, and British Pat. No. 1,352,464.

BRIEF DESCRIPTION OF THE INVENTION

This invention relates to a class of substituted amides and to their use as miticides when used in a miticidally effective amount. More specifically, this invention relates to N-t-butyl-α-trichlorophenoxybutyramides having the formula

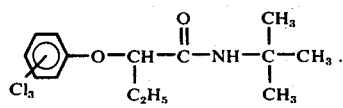

By "miticidally effective amount" is meant the amount of the herein disclosed miticidal compounds which when applied to the habitat of mites in any conventional manner will kill or substantially injure a significant portion of the population thereon.

The closest prior art concerning substituted phenoxyalkylamides consists of the French and British Patents cited above. The French Patent discloses amides with methyl, ethyl, and allyl substitutions on the nitrogen atom in place of the t-butyl radical of the compounds of the present invention. The British Patent discloses amides which differ from the compounds of the present invention by the substitutions on the phenyl ring, and which show no miticidal activity.

DETAILED DESCRIPTION OF THE INVENTION

The compounds of the present invention are prepared by the following general method:

Reaction No. 1

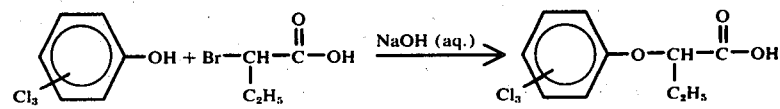

A slight molar excess of 50% aqueous NaOH is added to a mixture of a molar amount of the phenol and a slight molar excess of the acid. An organic solvent is added and the solution is washed and acidified. The product acid is then recovered from the organic phase.

Reaction No. 2

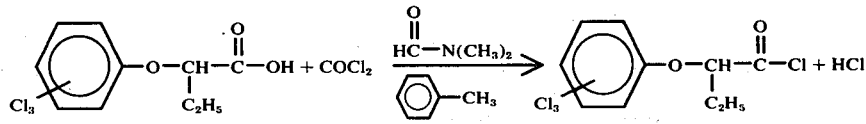

A slight molar excess of phosgene is introduced into a slurry of a molar amount of the acid in toluene, to which a small amount of dimethyl formamide has been added. The system is purged of excess phosgene and HCl, and the solvent is evaporated to leave the acid chloride.

Reaction No. 3

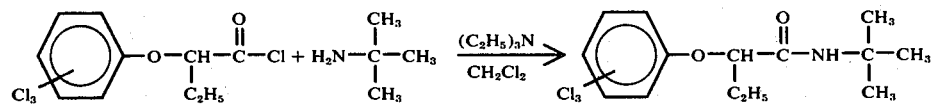

The acid chloride is added to a dichloromethane solution containing both the t-butylamine and the triethylamine at 10–15° C. The product is subsequently washed and recovered from the organic phase.

The examples used herein are illustrative of the method of preparation of the compounds of the invention.

EXAMPLE I
N-t-butyl-α-(2,3,5-trichlorophenoxy)butyramide.

Compound No. 1 in Table I below) 44.0 g (0.55 mole) of 50% aqueous NaOH was added to a mixture of 42.5 g (0.22 mole) of 2,3,5-trichlorophenol and 43.4 g (0.26 mole) of α-bromobutyric acid, with rapid stirring at an initial temperature of 15° C. The temperature rose to 45° C over the course of the addition and was held between 15° C and 45° C with a cold bath. After the addition of the NaOH, the cold bath was removed and the mixture was heated to 110° C for 15 minutes. Then 50 ml water, 53 ml perchloroethylene, and 42 ml concentrated HCl were added and the mixture was heated to 85° C. The mixture was then phase-separated and the organic layer was cooled. The product, α-(2,3,5trichlorophenoxy)butyric acid, separated on cooling and was removed by filtration to give 43.1 g (69.1% yield) of a solid, m.p. 106°-114° C.

A slurry of 50.3 g (0.18 mole) of α-(2,3,5-trichlorophenoxy)butyric acid in 80 ml toluene to which 0.2 ml dimethylformamide had been added was placed in a 500 ml flask fitted with a gas-inlet tube, a stirrer, a thermometer, and a dry ice-isopropyl alcohol condenser. The flask was heated to 60° C. 22 g (0.23 mole) phosgene was passed into the mixture at a moderate rate. The dry ice condenser was then removed and replaced with a water-cooled condenser. Excess phosgene and HCl were removed by an argon purge at 60° C. The solution was then cooled, and the solvent was removed in vacuum to leave 43.4 g (80% yield) of an oil, α-(2,3,5-trichlorophenoxy)butyryl chloride.

8.0 g (0.03 mole) of the acid chloride was added dropwise to a mixture of 2.6 g (0.04 mole) of t-butylamine and 3.6 g. (0.04 mole) of triethylamine in 100 ml of methylene chloride at 10–15° C. Some cooling in an ice bath was necessary to maintain the temperature. After the addition of the acid chloride, the mixture was allowed to come to room temperature. The product was then washed with 100 ml portions of water, dilute HCl, 5% $Na_2CO_3$ solution, and water again. The organic phase was dried over magnesium sulfate and the solvent was removed in vacuum to leave 10.0 g (99% yield) of the solid product, m.p. 151°-153° C, identified by infrared spectroscopy as N-t-butyl-α-(2,3,5-trichlorophenoxy)butyramide.

EXAMPLE II
N-t-butyl-α-(3,4,5-trichlorophenoxy)butyramide.

Compound No. 2 in Table I below)

50.8 g (0.63 mole) of 50% aqueous sodium hydroxide was added to a mixture of 50 g (0.25 mole) of 3,4,5-trichlorophenol and 50 g (0.30 mole) of α-bromobutyric acid, with rapid stirring at an initial temperature of 15° C. The temperature of the mixture was held below 45° C by a cold water bath. After the addition of the NaOH, the cold bath was removed and the mixture was heated at 110° C for 15 minutes. Then 62 ml water, 125 ml perchloroethylene and 50 ml concentrated HCl were added, and the mixture was heated to 85° C. The mixture was then phase-separated and the organic layer was cooled. The product, α-(3,4,5-trichlorophenoxy)butyric acid, separated on cooling was removed by filtration to give 54.2 g (76% yield) of a solid, m.p. 115°-118° C.

A slurry of 54.2 g (0.19 mole) of α-(3,4,5-trichlorophenoxy)butyric acid in 75 ml toluene to which 0.2 ml dimethyl formamide had been added was heated to 60° C in a 500 ml flask fitted with a gas-inlet tube, a stirrer, a thermometer, and a dry ice-isopropyl alcohol condenser. 22.0 g (0.23 mole) of phosgene was passed into the mixture at a moderate rate. The dry ice condenser was then removed and replaced with a water-cooled condenser. Excess phosgene and HCl were removed by an argon purge of the solution at 60° C. The solution was then cooled and the solvent was removed in vacuum to leave 54.9 g (95.6% yield) of a liquid, $n_D^{30}$ 1.5506, which was α-(3,4,5-trichlorophenoxy)butyryl chloride.

8.0 g (0.03 mole) of the acid chloride was added dropwise to a mixture of 2.1 g (0.03 mole) of t-butylamine and 3.2 g (0.03 mole) of triethylamine in 100 ml methylene chloride at 10°-15° C. The mixture was allowed to come to room temperature and then washed with 100 ml portions of water, dilute HCl, 5% $Na_2CO_3$ solution, and water again, to isolate the product. The organic phase was dried over magnesium sulfate and the solvent was removed in vacuum to leave 7.3 g (71.9% yield) of the solid product which was identified by infrared spectroscopy as N-t-butyl-α-(3,4,5-trichlorophenoxy)butyramide, m.p. 136°-138° C.

Other compounds, such as Compound No. 3 in the following table, can be prepared in a manner analogous to that shown in the examples above, starting with the appropriate materials. The compounds in the table are representative of those embodied in the present invention. Compound numbers have been assigned to them for purposes of identification throughout the balance of the specification.

TABLE I

| COMPOUND NUMBER | COMPOUND | MELTING POINT |
|---|---|---|
| 1 | 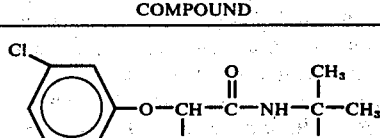 | 151–153° C |
| 2 | 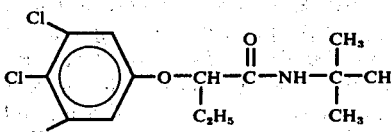 | 136–138° C |

TABLE I-continued

| COMPOUND NUMBER | COMPOUND | MELTING POINT |
|---|---|---|
| 3 | ![structure] 2,3,4-trichlorophenyl compound | 126–128° C |

Compound 3 structure: Cl, Cl, Cl trisubstituted phenyl—O—CH(C₂H₅)—C(=O)—NH—C(CH₃)₂—CH₃

Miticidal activity of each of the above compounds on the two-spotted mite [*Tetranychus urticae* (Koch)] was evaluated as follows:

Pinto bean plants (Phaseolus sp.), approximately 10 cm tall, are transplanted into sandy loam soil in 3-inch clay pots and thoroughly infested with two-spotted mites of mixed ages and sexes. Twenty-four hours later the infested plants are inverted and dipped for 2–3 seconds in 50–50 acetone-water solutions of the test chemicals. Treated plants are held in the greenhouse, and seven days later mortality is determined for both the adult mites and the nymphs hatching from eggs which were on the plants at the time of treatment. Test concentrations range from 0.05% down to that at which 50% mortality occurs (LD-50).

The following is a table of the results of the above test procedures indicating the effective concentration at which LD-50 control effect was achieved.

TABLE II

Effective Concentration on Two-Spotted Mite [Tetranychus urticae (Koch)]

| COMPOUND NUMBER | Post-Embryonic (%) | Eggs (%) |
|---|---|---|
| 1 | .005 | .03 |
| 2 | .03 | .03 |
| 3 | .05 | .05 |

Neither the examples nor the tables above are intended to limit the invention in any manner.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in miticide preparations. One such composition can contain either a single miticidally active compound or a combination of miticidally active compounds. The miticide compositions of this invention can contain as adjuvants organic solvents such as sesame oil, xylene, or heavy petroleum; water; emulsifying agents; surface active agents; talc; prophyllite; diatomite; gypsum; clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence such as light, or by some physiological action which the compound induces when it is ingested into the body of the pest.

The precise method in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

What is claimed is:

1. A compound having the formula

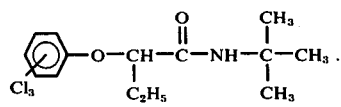

2. A compound according to claim 1 in which the chlorine atoms occupy the 3-, 4-, and 5-positions on the phenyl ring.

3. A compound according to claim 1 in which the chlorine atoms occuply the 2-, 3-, and 5-positions on the phenyl ring.

4. A compound according to claim 1 in which the chlorine atoms occupy the 2-, 3-, and 4-positions on the phenyl ring.

5. A method of controlling mites comprising applying to said mites a miticidally effective amount of a compound having the formula

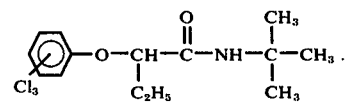

6. A method according to claim 5 which the chlorine atoms occupy the 3-, 4-, and 5-positions on the phenyl ring.

7. A method according to claim 5 in which the chlorine atoms occupy the 2-, 3-, and 5-positions on the phenyl ring.

8. A method according to claim 5 in which the chlorine atoms occupy the 2-, 3-, and 4-positions on the phenylring.

* * * * *